United States Patent [19]

Tomer

[11] Patent Number: 5,763,201
[45] Date of Patent: Jun. 9, 1998

[54] FLOW CYTOMETRY ASSAY FOR HEPARIN-INDUCED THROMBOCYTOPENIA

[75] Inventor: Aaron Tomer, Atlanta, Ga.

[73] Assignee: Emory University, Atlanta, Ga.

[21] Appl. No.: 697,960

[22] Filed: Sep. 3, 1996

Related U.S. Application Data

[63] Continuation-in-part of Ser. No. 596,966, Feb. 5, 1996, abandoned.

[51] Int. Cl.$^6$ .................................................. G01N 33/53
[52] U.S. Cl. .................. 435/7.21; 435/7.24; 435/975; 436/507
[58] Field of Search .......................... 435/7.21, 7.24, 435/975; 436/507

[56] References Cited

U.S. PATENT DOCUMENTS

| | | | |
|---|---|---|---|
| 5,246,832 | 9/1993 | Michelson et al. | 435/7.2 |
| 5,466,582 | 11/1995 | Amiral | 435/7.9 |
| 5,529,902 | 6/1996 | Kottke et al. | 435/7.21 |
| 5,627,036 | 5/1997 | Rsutelingsperger | 435/7.21 |

OTHER PUBLICATIONS

Information sheet on LOVENOX (enoxaparin sodium) injection, Rhône-Poulenc Rorer Pharmaceuticals Inc., Collegeville, Pa.

Kelton, J.G. et al., "Clinical usefulness of testing for a heparin–dependent platelet–aggregating factor in patients with suspected heparin–associated thrombocytopenia," *J. Lab. Clin. Med.*, (1984) 103(4):606–612.

Sheridan, D. et al., "A Diagnostic Test for Heparin–Induced Thrombocytopenia," *Blood* (1986) 67(1):27–30.

George, J.N. et al., "Platelets", Section III: Hemostasis, Hematology 1994, Education Program, *Am. Soc. Hematology*, (Dec. 2–6, 1994), pp. 66–74.

McEver, R.P. and Martin, M.N., "A Monoclonal Antibody to a Membrane Glycoprotein Binds Only to Activated Platelets," *J. Biol. Chem.*, (1984) 259(15):9799–9804.

Shattil, S.J. et al., "Changes in the Platelet Membrane Glycoprotein IIb•IIIa Complex during Platelet Activation," *J. Biol. Chem.* (1985) 260(20):11107–11114.

Thiagarajan, P. and Tait, J.F., "Binding of Annexin V/Placental Anticoagulant Protein I to Platelets," *J. Biol. Chem.* (1990) 265(29):17420–17423.

Tomer, A., "Reduced Predisposition to Thrombosis in Sickle Cell Disease (SCD) Patients Treated with Dietary n–3 Fatty Acids (n–3FA)," *Blood* (1995) 86(10), Suppl. 1:1182.

Wall, J.E. et al., "A flow cytometric assay using mepacrine for study of uptake and release of platelet dense granule contents," *British J. Haematology* (1995) 89:380–385.

Kelton et al., *Blood*, 83, 3232–3239, 1994.

Lee et al., *Brit. Jour. Haemat.*, 95, 724–731, 1996.

*Primary Examiner*—David Saunders
*Attorney, Agent, or Firm*—Greenlee, Winner and Sullivan, P.C.

[57] ABSTRACT

The present invention relates to a flow cytometry assay for the determination of heparin-induced thrombocytopenia. This method (a) detects in a plasma sample the presence of anti-heparin antibodies which react with platelets in the presence of heparin to produce activated platelets, (b) quantitates by flow cytometry the presence of such activated platelets in the plasma sample, and (c) correlates the presence of activated platelets with a diagnosis of HIT for the patient. In addition, the flow cytometry assay of the invention is also useful in assessing the compatibility of a heparin-like molecule for use as an alternate therapy for patients with heparin-induced thrombocytopenia. In addition, the invention contemplates a mepacrine release assay with flow cytometry for the detection of heparin-induced thrombocytopenia and for the assessment of compatibility of heparin-like molecules in patients diagnosed with heparin-induced thrombocytopenia.

38 Claims, 6 Drawing Sheets

FLOW CYTOMETRY ASSAY FOR HEPARIN-INDUCED THROMBOCYTOPENIA

RELATEDNESS OF THE INVENTION

The subject application is at continuation-in-part of copending U.S. application Ser. No. 08/596,966, filed on Feb. 5, 1996, and now abandoned, which is incorporated herein in the entirety by reference.

FIELD OF THE INVENTION

This invention relates to a diagnostic assay for heparin-induced thrombocytopenia (HIT). Specifically, the present invention provides a highly sensitive and specific flow cytometric (FCM) assay useful for immediate determination of HIT.

BACKGROUND OF THE INVENTION

Heparin administration is the standard antithrombotic therapy indicated for acute venous thrombosis, for prophylaxis in the post surgical (especially orthopedic) and immobile patient, and for flushing of intravenous lines to maintain patency. Approximately 5% (range up to 30%) of patients treated with heparin develop immune-mediated thrombocytopenia (HIT) which may be complicated by either bleeding (as a consequence of decreased platelet count) or arterial and venous thrombosis due to intravascular platelet clumping. This complication occurs in as many as 20% of patients with HIT and may result in serious morbidity and death in about 50% of the cases. Because the diagnosis of HIT poses a serious problem of management, a rapid and reliable determination of HIT is clinically important. Treatment with heparin in the face of HIT results in serious aggravation of the hemostatic complications, hence, heparin therapy in that case should be discontinued. On the other hand, discontinuation of heparin may expose the patient, who requires antithrombotic therapy, to excessive risk of thrombosis since no alternate therapy with immediate and effective antithrombotic capacity is presently available. Moreover, the alternate therapies, such as low-molecular weight heparin or heparinoids, may not be compatible because of potential crossreaction with the anti-heparin antibodies, resulting in further aggregation of HIT. Thus, a rapid and highly reliable affirmative test for HIT is required for correct management decisions. Unfortunately, despite an urgent need thereof, no such test is routinely available to effectively support management decisions and consequently, the initial diagnosis is presently being made on a clinical basis only.

According to the literature the incidence of HIT in patients receiving therapeutic doses of heparin is approximately 5% (range up to 30%). This estimate is somewhat lower in patients receiving heparin in prophylactic doses or in flush solutions (conservative estimate of 2.5%). The incidence of HIT, however, is underestimated. Firstly, because of the lack of a routine test for HIT, only patients who develop significant thrombocytopenia are usually considered for HIT. Secondly, sudden thrombotic events such as myocardial infarction, peripheral arterial thrombosis, and pulmonary emboli are often not recognized as a complication of heparin because of the patient's underlying illnesses. Furthermore, some patients with heparin-induced antibodies have thrombosis in the absence of thrombocytopenia. Thus all patients receiving heparin who develop thrombosis should be suspected and tested for HIT. In addition, as low-molecular weight heparin is being recommended for prophylaxis for out-patient (a single, subcutaneous dose/day, requiring no monitoring), the incidence of HIT can be expected to increase. Thus, it is reasonable to anticipate that the request for a reliable routine test for HIT will increase significantly.

The method of the present invention obviates the difficulties and limitations that are inherent in the prior art methods that are currently used for detection of HIT. Many of the prior art methods of detecting HIT detect the appearance of antibodies directed against platelets, or the immune complex formed thereof, or a transport function dependent thereon, in the presence of heparin. According to Admiral [U.S. Pat. No. 5,466,582 issued Nov. 14, 1995], "these biological assays are either (a) rather insensitive or rather unreliable or (b) if they are sensitive, lengthy to carry out." For example, a test to diagnose HIT was previously developed based on the finding that a heparin-dependent platelet-aggregating factor appeared in sera of patients with HIT [Fratantoni et al. (1975) Blood 45:396]. However, this promising platelet aggregation assay was found to be insensitive and non-specific, giving positive results in some patients without HIT and negative results in some patients with HIT [Kelton et al. (1984) J. Lab. Clin. Med. 103:606]. Problems with both sensitivity and specificity seriously compromised the usefulness of this assay for diagnostic use.

A second assay, a serotonin release assay (SRA), was developed from the observation that sera from patients with HIT initiated platelet aggregation and secretion at therapeutic, but not at high, concentrations of heparin. This assay, still regarded as the gold-standard assay for HIT, measures the release of radiolabeled serotonin from platelets at two heparin concentrations, since sera from patients with HIT caused release of serotonin at therapeutic but not at high concentrations of heparin. This test has a high specificity (99%), is very sensitive, and indicates a direct correlation between a positive test result and the clinical likelihood of a patient having HIT [Sheridan et al. (1986) Blood 67:27–30]. The serotonin release assay is a more sensitive test of platelet activation than was the aggregation assay. However, certain disadvantages are associated with the serotonin release assay; for example, (a) the use of radiolabeled ($^3$H or $^{14}$C) serotonin is required; (b) the assay can be performed only by research or specialized laboratories which carry a license for handling such radioactive materials; and (c) the need to perform the diagnostic serotonin release assay in a licensed laboratory, even for clinical use, denies immediacy for diagnosis of HIT and provides, instead, only retrospective confirmation [George et al. (1994) American Society of Hematology, Education Program, Nashville, Tenn., December 2–6].

An enzyme-linked immunosorbent assay (ELISA) is also currently proposed for use in the detection of HIT by measuring the presence of heparin-Platelet Factor 4-induced antibodies in plasma. Presently, kits for ELISA determination of HIT are currently available only for research purposes (e.g., American Bioproducts Co, Parsippany, N.J.). Although this method measures the presence in test plasma of antibodies that react with heparin-PF4 complexes, this assay is unable to establish a cause-result relationship that relates the presence of antibodies to platelet destruction and thrombocytopenia. The presence per se of antibodies that are immuno-reactive in vitro with heparin-Platelet Factor 4 complexes may or may not be indicative of the presence of HIT. The ELISA method detects only the presence of antibody, irrespective of its pathophysiologic significance. For example, in a related medical case, although up to 36% of patients taking α-methyldopa develop anti-red cell antibodies, only less than 1% exhibit cell destruction with hemolytic anemia [*Hematology*, 5th ed. (1985) W. J.

Williams, E. Beutler, A. J. Erslev and M. A. Lichtman, eds., New York, McGraw-Hill]. Thus, a patient being evaluated for HIT requires that the HIT assay method clearly determine not only the presence of antibodies to a heparin-platelet complex, but also demonstrate that these antibodies are directly relevant to the development of thrombocytopenia.

In addition, assays such as the ELISA are time-consuming, costly and thus are normally not performed for single determinations but samples are accumulated with time to be assayed concurrently as a multiple sample assay.

In contrast to existing prior art methods, the method of the present invention, the flow cytometry assay, is independent of the use of a radiolabeled marker; it provides a high specificity and a sensitivity greater than the serotonin release assay; and in contrast to the ELISA, it is a functional assay for detection of HIT. This method, by reproducing the in vivo pathophysiologic process of HIT, measures specifically platelets that are activated (and consequently destroyed), wherein the activation of platelets is dependent on heparin and test plasma antibodies and wherein the activation of platelets by heparin and test plasma antibodies is diagnostic evidence of in vivo HIT. Additional advantages of the flow cytometry method in comparison to prior art methods are:

(a) the ease of carrying out the flow cytometry assay, such as:
  (i) using readily available reagents,
  (ii) employing standard flow cytometric equipment available at any medical center, and
  (iii) requiring only standard, and not special, technical expertise;
(b) the rapidity and reliability of this assay as a diagnostic assay for HIT which
  (i) is available for a therapeutic decision within 1.5 to 2 hours, and
  (ii) is cost-effective and can be performed for a single case as well as for multiple cases; and
(c) the ability to determine the effectiveness and compatibility of alternate therapy, such as low molecular weight heparin or heparinoids, which might crossreact with the anti-heparin antibodies and cause HIT.

In comparing the various methods for diagnosis of HIT, the functional assays are considered clinically superior to immune-detection assays, since the latter detect only the presence of antibodies without establishing a cause-effect relationship with platelet destruction. Therefore, the immune detection assay cannot be directly related to clinical settings. In a recent study of ELISA vs. SRA (serotonin release assay), 22% of samples were found positive with the immune-assay but negative with the functional one [Arepally et al. (1995) Am. J. Clin. Pathol. 104:648–654]. As remarked by the authors of the study, "Some patients exposed to heparin may form low-affinity drug-dependent antibodies that . . . may have little correlation with the pathologic activity in vivo". Thus, the authors concluded that "positive ELISA results of this magnitude cannot in and of themselves be considered to provide unequivocal confirmation of the diagnosis of HIT. Performance of the SRA may provide confirmatory evidence in such cases". These remarks may be further highlighted by the observations [Kelton et al. (1988) Blood 72:925; Visentin et al. (1994) J. Clin. Invest. 93:81–88] that some patients with positive SRA may not have antibodies detected by immunologic assays. In contrast, the functional flow cytometry assay can effectively provide the necessary information correlating the presence of antibodies with platelet activation.

SUMMARY OF THE INVENTION

The present invention provides a method for diagnosing a condition of heparin-induced thrombocytopenia (HIT) in a patient treated with heparin by testing the patient's plasma in the presence of heparin for its ability to activate platelets, the ability to activate platelets in the presence of heparin being diagnostic of the presence of HIT.

The method of the invention provides a flow cytometry assay for the detection of HIT in a patient treated with heparin. This invention is based on the discovery that plasma from a patient with HIT is capable of activating platelets in vitro in the presence of heparin and that these activated platelets can be specifically labeled and therewith specifically detected with flow cytometry.

This flow cytometry method provides a functional assay for HIT by measuring the response of platelets to a patient's plasma in the presence of heparin. If anti-heparin antibodies are present in the patient's plasma sample, interaction of the anti-heparin antibodies with platelets in the presence of heparin will result in the activation of platelets. The experimental conditions of the assay reproduce the pathophysiologic phenomenon of a patient with HIT wherein a heparin immune complex interacts with platelets resulting in platelet activation and their consequent destruction.

In the flow cytometry method, platelets are obtained from whole blood as platelet rich plasma by gentle centrifugation. Further procedural manipulations of the platelets are avoided in order to prevent spontaneous activation of the platelets. The assay of the invention detects under experimental conditions the manifestation of activated platelets induced by heparin immune complex, an event which correlates with in vivo HIT. In this assay, the manifestation of activated platelets induced by heparin immune complex is detected with a highly sensitive probe interacting with, for example, the prothrombinase-binding sites on the anionic phospholipids exposed on the surface membrane upon activation. This functional method to detect HIT is a departure from current, art-standard ELISA methods which detect specifically only the immune reaction comprising HIT antibody, heparin and platelet antigen, a measurement which may or may not correlate with the observed condition of thrombocytopenia.

The flow cytometry method of the invention includes the steps of obtaining a plasma sample of a patient suspected of having HIT, interacting said plasma sample with platelets in the presence of heparin, further incubating the reaction mixture with a first labeled compound capable of specific binding to platelets and with a second labeled compound that binds specifically to activated platelets, determining with flow cytometry the level of the second label identifying activated platelets and diagnosing a condition of HIT for said patient where the level of labeled activated platelets in the patient plasma is elevated compared to a corresponding level of the second labeled compound in normal control plasma.

Although it is not mandatory to include the step of incubating the reaction mixture with a first labeled compound specific for platelets, the inclusion of this step in the method of the invention is preferred. Enhanced sensitivity was obtained for the flow cytometry assay when the step of labeling platelets with a first labeled compound was included in the method than when the assay was performed with only one labeled compound, i.e., a labeled compound specific for activated platelets detected by flow cytometry.

The flow cytometry method provides a determination that thrombocytopenia is specifically induced by heparin. In specific embodiments, the plasma sample from a HIT suspected patient is reacted with platelets in the presence of different concentrations of heparin including (a) no heparin, (b) a therapeutic concentration of heparin ranging from approximately 0.01 to approximately 0.1 IU/ml and (c) a high concentration of heparin ranging from approximately 10 to approximately 1000 IU/ml. A "no heparin" control is included in the assay to exclude any direct effect of plasma on platelet activation and to confirm the necessity of heparin participation in the reaction. A "high concentration of heparin" control is included to confirm the immune-mediated mechanism of HIT (which requires the aggregation of antibodies by the large heparin molecules, a process that can be abolished by excessive (by approximately 1000-fold) addition of antigen) and to exclude a direct effect of free heparin on platelet activation. In preferred embodiments, heparin is present in the assay at therapeutic concentrations of 0.1 and 0.3 IU/ml and at high concentrations of 100 IU/ml.

In particular embodiments, it is preferred that the first labeled compound be a labeled antibody to a platelet surface protein and, more preferably, an antibody to the platelet specific glycoprotein IIb/IIIa labeled with phycoerythrin or fluorescein isothiocyanate. In addition, it is preferred that the second labeled compound be a labeled compound specific for activated platelets, i.e., for a specific platelet surface membrane determinant that appears and correlates with the activation of platelets. It is equally preferred that the second labeled compound bind with high affinity to activated platelets, for example, with increased binding of over 300 fold for activated platelets compared to resting state platelets, and it is highly preferred that annexin V, especially a recombinant human annexin V that is directly labeled with fluorescein isothiocyanate or phycoerythrin, or otherwise distinguishably labeled for use with a first labeled compound, be utilized as the second labeled protein.

This invention contemplates that the choice of a first and a second labeled compound be based on (a) binding affinity of labeled compound to platelets and (b) the ability to distinctly detect the signal of each of the two labels in flow cytometry. It is preferred that the signal of the first label be separable from and distinguishable over that of the second label with flow cytometry. Accordingly, this invention prefers the use of such labels as phycoerythrin or fluorescein isothiocyanate in combination and interchangeably, e.g., a phycoerythrin or fluorescein isothiocyanate labeled antibody to platelet glycoprotein IIb/IIIa as the first labeled compound and, respectively, a directly fluoresceinated or phycoerythrin labeled recombinant human annexin V as the second labeled compound.

Further, the instant invention provides a complementary test which may be carried out in combination with the flow cytometry assay in order to obtain direct evidence for an antibody-mediated mechanism responsible for platelet activation. This test comprises the step of detecting in sample of the patient plasma the presence of human immunoglobulins that are available for the formation of a heparin-immune complex responsible for platelet activation. In a specific embodiment of the invention, an aliquot of the patient plasma sample is pre-incubated with antibodies against human immunoglobulins, e.g., anti-human IgG and/or IgM. The effect of the pre-incubation of patient HIT plasma with human immunoglobulin is to neutralize the effect of HIT patient antibodies which otherwise induced platelet activation in the presence of heparin. Inclusion of this pre-incubation step in the flow cytometry method of the invention constitutes a complementary test to confirm the presence in a sample of patient plasma of immunoglobulin available for the formation of a platelet-heparin-immune complex.

Further, the flow cytometry method of the present invention provides an assay to assess the compatibility of a heparin-like molecule for use as an alternate therapy for patients having HIT. In a patient with HIT, heparin-like molecules, such as low molecular weight heparin, heparinoids and the like, may be considered as alternate therapies, if anti-heparin antibodies in the patient's blood are shown not to crossreact with these heparin-like molecules. The method of the invention allows a potential heparin-like therapeutic to be tested with flow cytometry for its ability to activate platelets in the presence of the patient's plasma. The ability to activate platelets in the presence of a heparin-like molecule is diagnostic of incompatibility of that heparin-like molecule as an alternate therapy to heparin. Again, the flow cytometry assay measures in vitro a function (platelet activation and subsequent destruction) that occurs in vivo in the physiological etiology of HIT.

Thus, the present invention provides a flow cytometry assay which can be utilized expeditiously and simultaneously for the detection of not only the presence of HIT but also the compatibility of an alternate therapy under consideration for an HIT patient. According to the method of the invention, aliquots of a patient plasma sample can be assayed at the same time and under the same conditions for the detection of HIT as well as for the detection of the patient's ability to tolerate a heparin-like molecule in lieu of heparin. The ability to obtain results for both detection assays simultaneously and within two hours of obtaining the plasma sample permits not only an immediate diagnosis of HIT but also enables a necessary and correct management decision to be made for the continued care of the patient with HIT.

In addition, the present invention provides a mepacrine release assay with flow cytometry for the detection of HIT and also for the assessment of a heparin-like molecule as an alternate therapy in patients with HIT. Although the mepacrine assay is specific for HIT, it does not exhibit the high sensitivity of the flow cytometry assay of the present invention for detection of HIT.

DETAILED DESCRIPTION OF THE INVENTION

Figure 1:
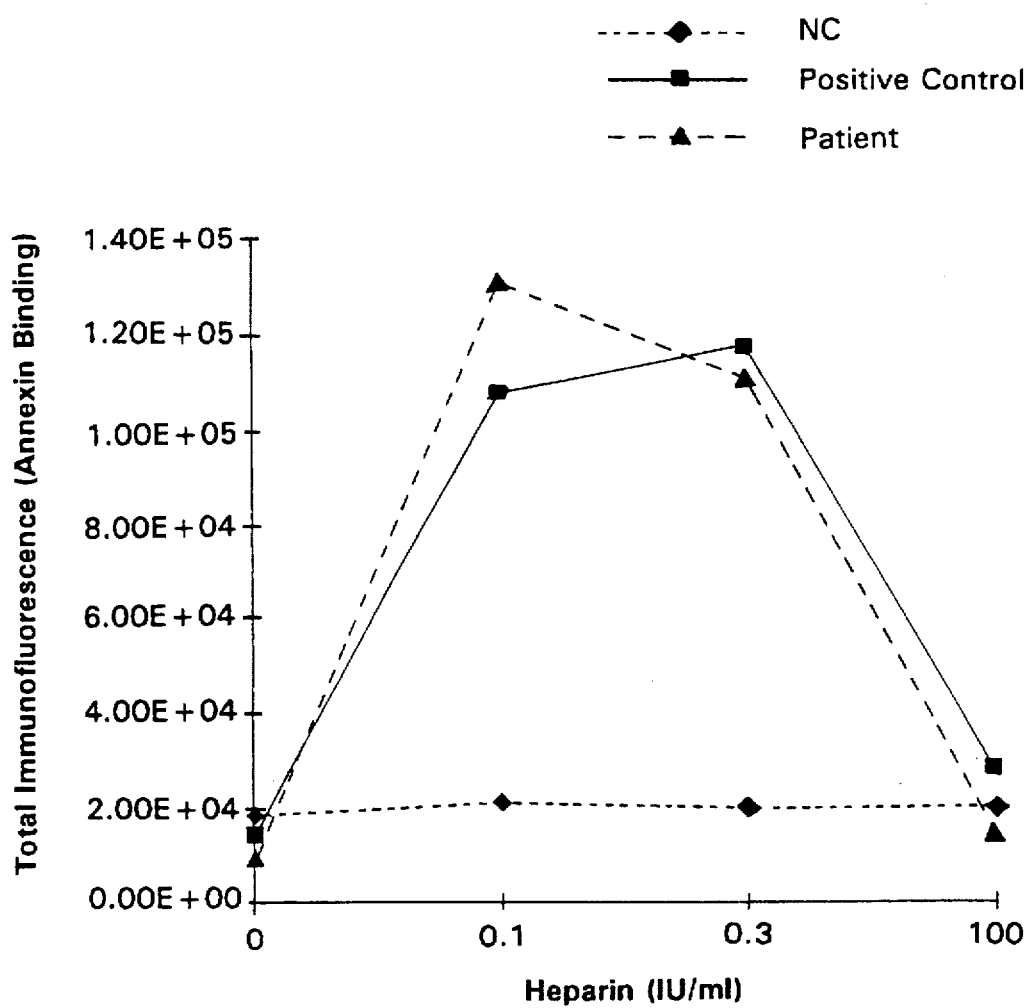
FIG. 1 demonstrates the relationship between the amount of immunofluorescence due to annexin V binding to activated platelets (ordinate) and the final concentration of heparin (abscissa). "NC" refers to normal controls wherein plasma samples are obtained from normal individuals. "Positive control" refers to a plasma sample from a patient previously diagnosed as having HIT. "Patient" refers to a plasma sample from a patient suspected of having HIT.
Figure 2A:
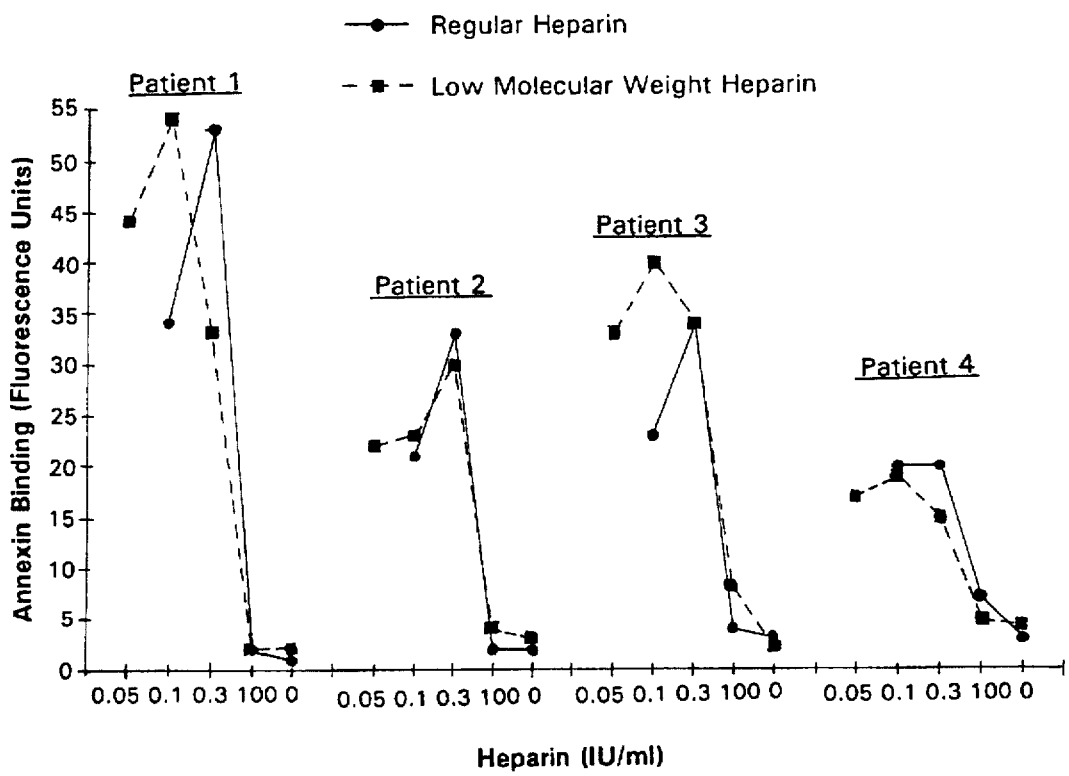
FIGS. 2A, 2B, 2C, 2D and 2E illustrate a comparison between standard heparin and low molecular weight heparin in the flow cytometry assay for the detection of HIT in plasma samples from sixteen different patients suspected of having HIT.
Figure 2B:
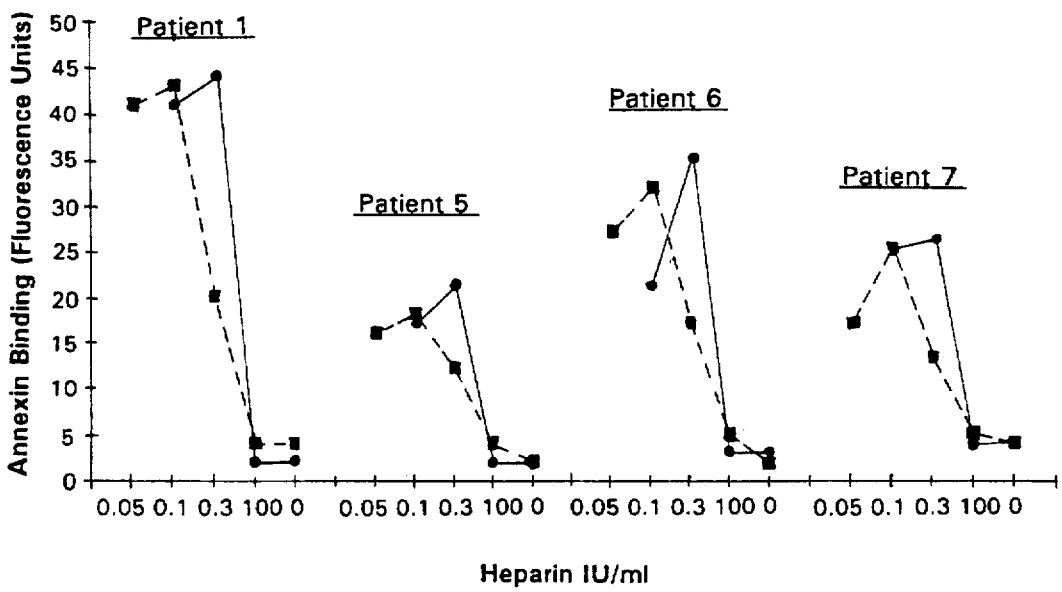
Figure 2C:
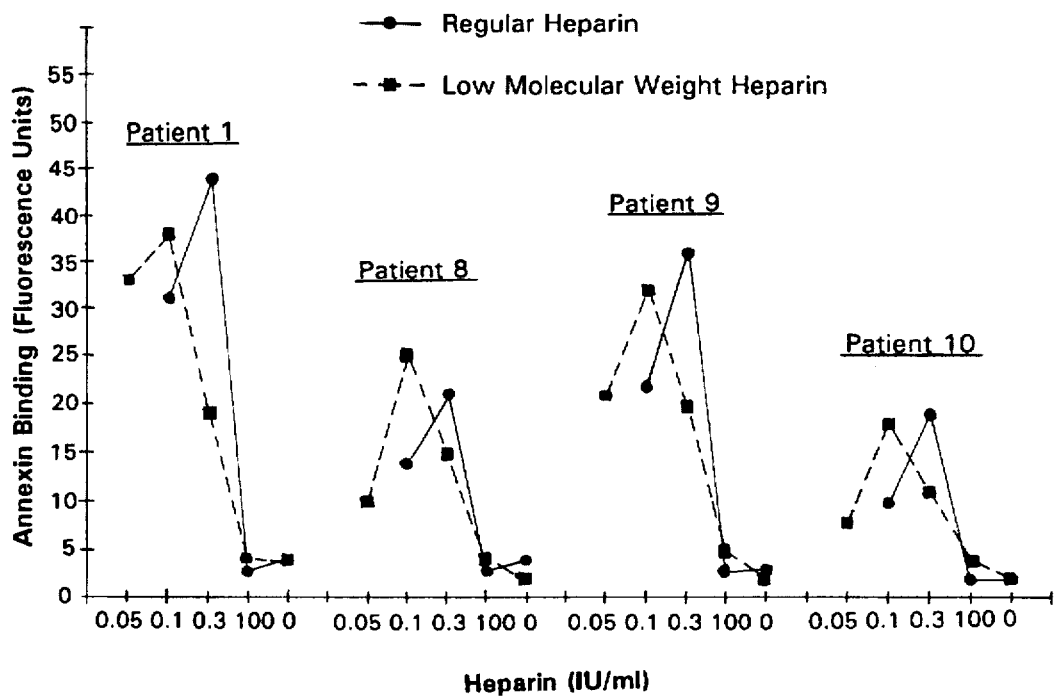
Figure 2D:
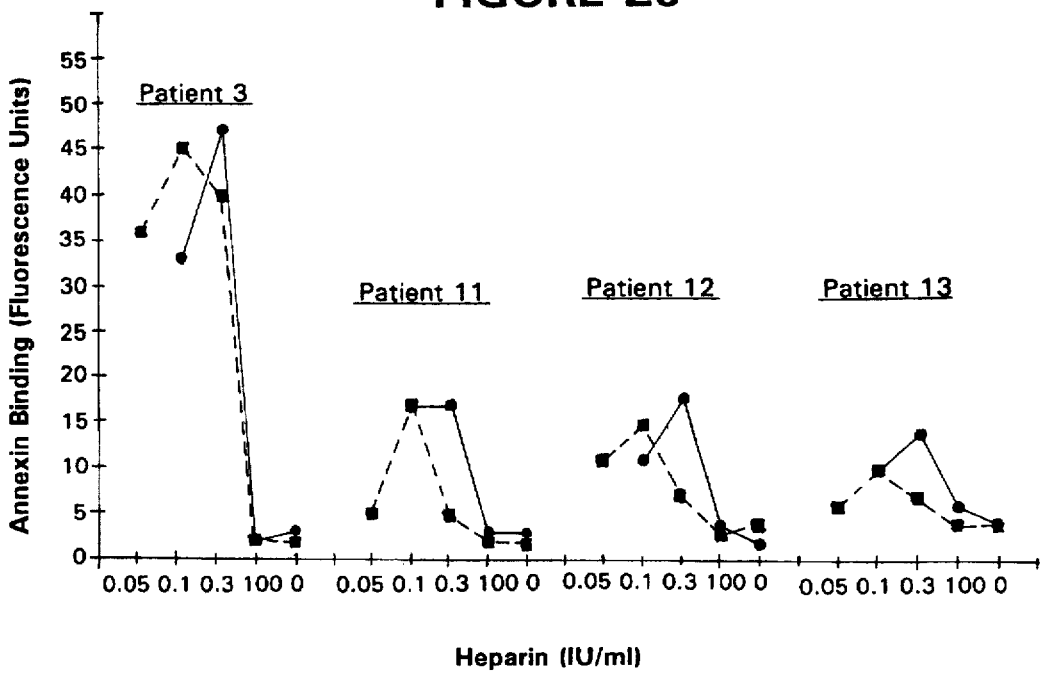
Figure 2E:
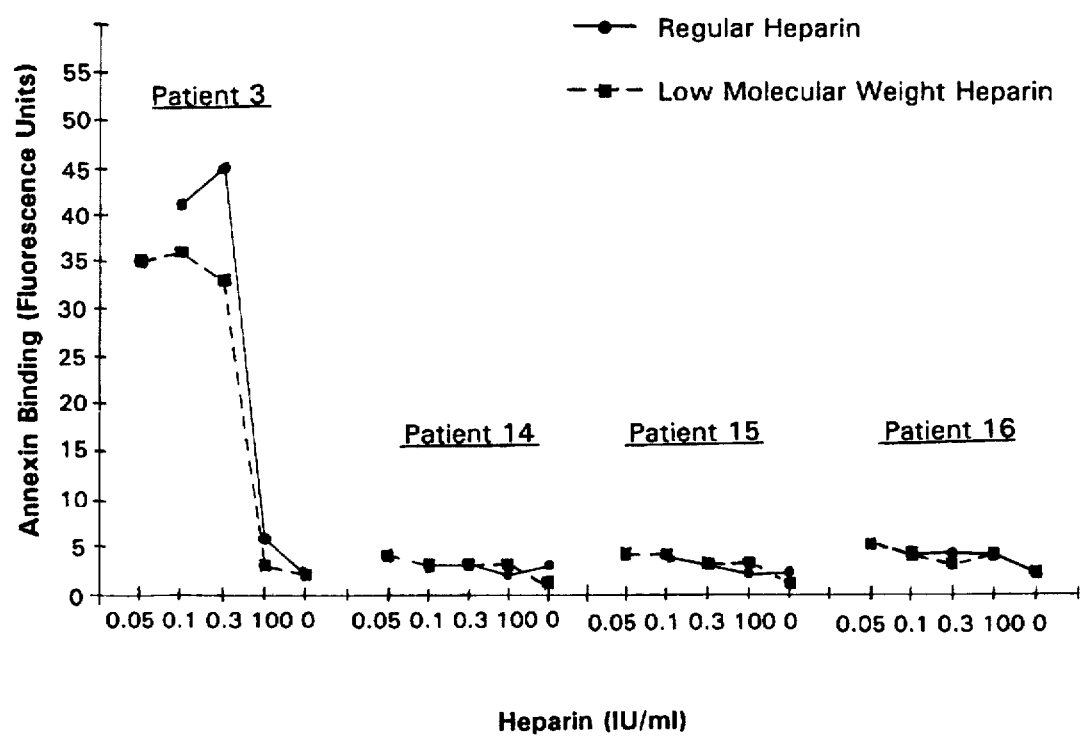

The following definitions are provided to remove any potential ambiguities as to the intent or scope of their usage in the specification and claims.

The term heparin as used herein refers to standard commercially available heparin and derivatives thereof. The term standard heparin encompasses a mixture of unfractionated heparin molecules having an average molecular weight of between about 8,000 and about 30,000 daltons or any subfraction thereof. In addition, it is contemplated that the term heparin as used herein encompasses biologically active heparin molecules that are isolated from a mammalian source, that are chemically modified, or that are partially or completely synthesized de novo. The term heparin derivatives encompasses salts of heparin, heparin fragments and the like.

The term therapeutic concentration of heparin as used herein refers to a concentration of heparin that is effective in inducing thrombocytopenia in vitro [see Sheridan et al. (1986) Blood 67:27-30]. A therapeutic concentration of heparin includes a range of concentrations from about 0.001 to about 1.0 IU/ml, preferably from about 0.01 to about 1.0 IU/ml, and more preferably from about 0.05 to about 0.5 IU/ml.

The term high concentration of heparin as used herein refers to a concentration of heparin that is greater than a therapeutic concentration of heparin and that is ineffective in inducing platelet activation in vitro, for example, heparin concentrations between about 10 and about 1000 IU/ml and preferably about 100 IU/ml [see Sheridan et al. (1986) supra].

The term heparin-like molecule as used herein refers to a molecule that possesses an anticoagulant activity and a chemical structure sufficiently similar to that of heparin such that said molecule is considered as a possible alternate therapy to a patient requiring heparin. A heparin like molecule includes, but is not limited to, a low molecular weight heparin, a heparin analogue, and the like. The term low molecular weight heparin includes heparin molecules having a molecular weight of less than 8,000 daltons. The term heparin analogue comprises heparinoids, such as hepramine and its salts, chondroitins and their salts, and the like.

The term activated platelets as used herein refers to platelets which are functionally transformed so as to be capable of adhesion or aggregation, platelet aggregate formation being dependent primarily on the GPIIb-GPIIIa complex [Harker et al. (1992) in Fuster, V., Verstraete, M. (eds.): Thrombosis in Cardiovascular Disorders, Philadelphia, W. B. Saunders CO., pp. 1–16; Ruggeri (1989) Circulation 80:1920–1922], which is a member of the integrin superfamily of adhesion receptors [Pytela et al. (1986) Science 231:1559–1562]. Other events may occur at the platelet surface on activation, including conformational changes in receptors occupied by ligands, as well as in platelet-bound ligands themselves, and expression of membrane constituents after granule secretion [e.g., p-selectin (CD62)], with the fusion of granule membranes to the platelet plasma membrane [McEver et al. (1984) J. Biol. Chem. 259:9799–9804; Shattil et al. (1985) J. Biol. Chem. 260:11107–11114]. Fully activated platelets express procoagulant activity. This activity is expressed via the exposure of anionic phospholipids (phosphatidylserine or phosphatidylcholine) on the surface membrane, which serve as binding sites for the prothrombinase complex (coagulation factors X, V and prothrombin), and markedly enhance (by $10^5$ fold) the generation of thrombin. The membrane procoagulant activity can be assessed by the binding of annexin V protein (a placental anticoagulant protein) to the prothrombinase-complex binding sites.

The term labeled compound as used herein refers to a compound that is labeled using any of a variety of labels and methods of labeling known in the art. Examples of types of labels encompassed by the present invention include, but are not limited to, radioisotopic labels (e.g., $^3H$, $^{125}I$, $^{131}I$, $^{35}S$, $^{14}C$, etc.), non-radioactive isotopic labels (e.g., $^{55}Mn$, $^{56}Fe$, etc.), fluorescent labels (e.g., a fluorescein label, an isothiocyanate label, a rhodamine label, a phycoerythrin label, a phycocyanin label, an allophycocyanin label, art O-phthaldehyde label, a fluorescamine label, etc.) for example, as in peridinin chlorophyll protein (PerCP), chemiluminescent labels, enzyme labels (e.g., alkaline phosphatase, horse radish peroxidase, etc.), protein labels, labels useful in radioimaging and radioimmunoimaging, etc.

The terms platelet-rich plasma or platelets as used herein refer to a standard preparation of platelets centrifuged at low speed from whole blood for use in the flow cytometry assay of the invention.

The term a negative condition of heparin-induced thrombocytopenia (HIT) as used herein refers to a diagnosis that is negative for heparin-induced thrombocytopenia, as determined by the flow cytometry method of the invention.

The term elevated compared to the corresponding level in normal plasma as used herein refers to the condition wherein the level of activated platelets in a patient's plasma as assessed by the fluorescence of bound annexin V is significantly higher, i.e., approximately 100% or more, than the level of corresponding activated platelets in a corresponding sample of normal plasma.

The term decreased compared to the corresponding level in normal control plasma as used herein refers to the condition wherein the level of fluorescence of mepacrine-containing platelets in a patient plasma sample is significantly decreased, i.e., approximately 50% or less; than the level of fluorescence for a corresponding sample of a normal control plasma.

The term normal control plasma or normal plasma as used herein refers to plasma from a normal individual without HIT.

The term room temperature as used herein refers to a preferred temperature of between 23° C. and 28° C. If the reaction is carried out at a temperature outside the preferred range, as may be desired in some laboratories, it would be necessary to experimentally re-establish the duration of time necessary for incubation of the reaction mixture under the new conditions.

The term annexin V as used herein refers to a placental anticoagulant protein reactive with prothrombinase-complex phospholipid membrane binding sites (anionic phosphatidylserine or phosphatidylcholine determinants exposed on a platelet surface following activation). This probe has been tested in two forms: (a) a native, purified protein (Dr. J. Tait, University of Washington, Seattle, Wash.) and (b) a human recombinant product (Dr. Toru Yokoyama, Kowa Co., Tokyo, Japan). The annexin V used in the experiments disclosed herein refers to a directly fluoresceinated (fluorescein isothiocyanate (FITC)-conjugated) human recombinant form, which has proved to be the most sensitive probe for detection of platelet activation with increased binding of over 300-fold compared to the normal resting platelet state.

The term annexin V fluorescence or annexin fluorescence as used herein refers to the specific green-fluorescence of annexin V used to measure the extent of binding of annexin V to activated platelets. Activated platelets exhibit enhanced binding of annexin V of over 300-fold in comparison to platelets at resting state.

The term glycoprotein IIb/IIIa antibody or anti-glycoprotein IIb/IIIa antibody or GPIIb/IIIa antibody or anti-CD41a antibody as used herein refers to an antibody directed against glycoprotein IIb/IIIa (CD41a), the most abundant functional receptor on the platelet surface (approximately 50,000/platelet). The anti-GPIIb/IIIa antibody preferred by this invention is the monoclonal antibody and, more preferably, the P2 clone. [Immunotech, Inc. (AMAC Co.), Westbrook ME]. The P2 monoclonal antibody reacts with high affinity against GPIIb/IIIa and constitutes a probe for the immunodetection of platelets in resting and activated states.

The term anti-GPIIb (CD41b) antibody as used herein refers to an antibody against the glycoprotein IIb (the CD41b receptor). It is a platelet specific probe, but inferior in sensitivity to the P2 antibody against GPIIb/IIIa.

The term anti-GPIIIa (CD61) antibody as used herein refers to an antibody against the glycoprotein IIIa (CD61). This subunit of GPIIb/IIIa is also expressed on monocytes as part of the vitronectin receptor ($\alpha V \beta_3$) and thus it is not platelet-specific. Further, the sensitivity of an anti-GPIIIa antibody as a probe for platelet identification is inferior to that of a P2 antibody probe.

The term anti-GPIb (CD42b) antibody as used herein refers to an antibody against the glycoprotein GPIb, a major receptor, CD42B, for the von Willebrand factor. It is specific for platelets, but the number of GPIb receptors expressed,is only about 30%–50% of that of GPIIb/IIIa, rendering the anti-GPIb antibody probe less sensitive compared to the P2 antibody probe.

The term anti-GPIV (CD36) antibody as used herein refers to an antibody against the glycoprotein GPIV (CD36) receptor which is highly expressed on platelets. However, since it is also expressed on monocytes, the GPIV antibody is not a platelet-specific probe.

The term an anti-human immunoglobulin preparation as used herein refers to a preparation consisting essentially of anti-human IgG or IgM or a combination thereof.

The present invention relates to a flow cytometry assay for the determination of thrombocytopenia of immune origin, induced specifically by heparin. This method (a) detects in a HIT-suspected patient plasma sample the presence of anti-heparin antibodies which react with platelets in the presence of heparin to produce activated platelets, (b) quantitates the presence of such activated platelets in the plasma sample, (c) correlates the presence of activated platelets with a diagnosis of HIT for the patient and (d) assesses compatibility of alternative therapy for heparin. The flow cytometry assay of the invention is a functional assay reproducing the in vivo pathophysiologic process of HIT by confirming the functional interaction of heparin immune-complex with platelets resulting in platelet activation and destruction.

The flow cytometry assay for the diagnosis of heparin-induced thrombocytopenia (HIT) is easily and rapidly carried out in any clinical laboratory under standard conditions using standard reagents and technology. A patient suspected of having HIT can be immediately diagnosed for the presence or absence of HIT with the FCM method of the invention. This method, by enabling a diagnosis to be made within approximately 1.5 to 2 hours after receiving a blood sample, allows an informed, critical decision to be made as soon as possible with respect to immediate therapeutic management of the patient.

According to the invention, the flow cytometry assay determines particularly the existence of a thrombocytopenia that is induced specifically by heparin. In a specific embodiment of the invention, aliquots of plasma from a patient suspected of having HIT were incubated with platelet-rich plasma and with different concentrations of heparin (none, one or more therapeutic concentrations and a high concentration). Under experimental conditions, heparin induction of thrombocytopenia is effected only at therapeutic concentrations of heparin (e.g., at approximately 0.1 and 0.3 IU/ml) and not at high heparin concentrations (e.g., at approximately 100 IU/ml). Therefore, assay controls containing zero heparin or a high concentration of heparin were included to ascertain (a) that a precondition in the plasma causing thrombocytopenia was not already in existence and (b) that the thrombocytopenia being measured was induced by heparin-associated immune complex formation. After a thirty to sixty minute incubation at room temperature (preferably at 25° C.), aliquots of each sample were further incubated for 15 to 30 minutes at room temperature (preferably at 25° C.) with (a) a first labeled compound capable of binding to platelets and (b) a second labeled compound capable of binding specifically to activated platelets. By standard flow cytometric analysis using a FACscan analyzer (Becton Dickinson, San Jose, Calif.) or other conventional model, a platelet population comprising both resting state and activated platelets was identified by the signal (label) of the first labeled compound, while the subpopulation containing only activated platelets was detected by the signal (label) of the second labeled compound.

Although it is not mandatory to include the step of incubating the reaction mixture with a first labeled compound capable of specific binding to platelets, it is preferred that this step be included in the flow cytometry assay in order to identify the population of platelets from other cell particles or contaminating debris and, hence, be used as an internal, independent index of the totality of platelets that are present in the resting state as well as in the activated state. In flow cytometry, a prior identification of the platelet population permits selection for same by an electronic gate and therefore allows the same platelet population to be analyzed for the second label specific for activated platelets. Enhanced sensitivity for the flow cytometry assay was obtained when the step of labeling platelets with a first labeled compound was included in the method than when the assay was performed with only one labeled compound, i.e., a labeled compound specific for activated platelets.

For identification of the total platelet population with flow cytometry, it was preferred that phycoerythrin-labeled antibody against platelet glycoprotein IIb/IIIa be used as the first labeled compound. In flow cytometry, platelets can be identified by light scatter and further distinguished from other blood elements and cell debris by a specific signal, e.g., immunofluorescence. This can be achieved by labeling with specific antibodies which interact with surface membrane receptors including: (a) glycoprotein (GP) IIb/IIIa (CD41a) complex or components thereof, e.g., GPIIb (CD41b) and GPIIIa (CD61), (b) GPIb (CD42b) and (c) GPIV (CD36), (thrombospondin receptor). Other receptors such as CD51, CD42 and GPIX (CD42A) may not be abundantly expressed and, therefore, show relatively low sensitivity when used as probes.

The anti-glycoprotein IIb/IIIa (CD41a) antibody, especially the P2 monoclonal antibody [P2 clone, Immunotech, Inc. (AMAC Co.), Westbrook, Me.] reacts with high affinity against GP|IIb/IIIa resulting in both a highly sensitive and highly specific interaction. The anti-GPIIb (CD41b) antibody also can be used as a specific probe for platelets; however, the commercially available probes have been found to be inferior in sensitivity to the P2 antibody against GPIIb/IIIa. Thus, the P2 antibody is the preferred probe for the imnunodetection of platelets in both resting and activated states. The anti-GPIIb (CD41b) and GPIb (CD42b) antibodies, although specific probes for platelets, are inferior in sensitivity to the P2 monoclonal antibody against GP' [IIb/IIIa. The anti-GPIIIa (CD61) and anti-GPIV (CD36) antibodies are not specific for platelets and, consequently, are inferior as probes in comparison to the P2 antibody.

There are several probes available for the detection of activated platelets. Many of these probes are specific to a particular receptor or membrane surface protein, while some of these probes bind more generally to the platelet membrane surface but only when the platelet is in a particular physiological state. In the method of the invention, directly fluoresceinated annexin V was utilized as the probe of choice for detection of activated platelets. Annexin V binds with high affinity to functionally activated platelets, e.g., to anionic phosphatidyl-serine and phosphatidylcholine determinants that appear on the transformed or activated platelet; annexin V does not exhibit such high affinity binding to normal resting state platelets [Thiagarajan et al. (1990) J. Biol. Chem. 265:17420–17423; Tomar et al. (1995) Blood 86(10), Suppl. 1:1182]. Other probes, especially those that act like annexin V in binding with high affinity to the activated platelet surface, can also be used according to the invention as a second labeled compound in the flow cytometry assay to determine the presence of activated platelets in plasma samples.

In the selection of a first and a second label, it is contemplated that such preferred labels as phycoerythrin and fluorescein thioisocyanate be used in combination and interchangeably, e.g., the use of a phycoerythrin or fluorescein isothiocyanate to label the first labeled compound and a fluorescein isothiocyanate or phycoerythrin, respectively, to label the second labeled compound. Whatever the choice of appropriate labels, it is necessary that the signal of the first label be separable from and distinguishable over that of the second label with flow cytometry.

Protein probes that were tested for utility in the detection of activated platelets comprised:

(a) monoclonal antibodies against the activated GPIIb/GPIIIa complex, e.g., PAC1 which competes with fibrinogen [Dr. S. Shattil, University of Pennsylvania, Philadelphia, PA]; anti-LIBS which interacts with the fibrinogen ligand to induce binding sites [Dr. E. Plow, Scripps Clinic and Research Foundation, La Jolla, Calif.]; anti-RIBS which interacts with an epitope expressed on platelet-bound fibrinogen [Dr. E. Plow, Scripps Clinic and Research Foundation, La Jolla, Calif.], etc.;

(b) monoclonal antibodies which detect platelet release reaction, e.g., S12, GE12 and GE6 [Biogen, Cambridge, Mass.] directed against p-selectin (CD62), an α-granule membrane protein translocated to the platelet surface following secretion, etc.; and (c) protein probes detecting platelet procoagulant activity with resultant generation of thrombin and promotion of thrombogenic activity, e.g., V261 monoclonal antibody against activated coagulation factor V fragment (Va) of the prothrombinase complex on the platelet surface [Dr. C. Esmon, Oklahoma Medical Research Foundation], annexin V, a placental anticoagulant protein reacting with prothrombinase-complex phospholipid membrane binding sites, and the tick anticoagulant peptide (TAP), an inhibitor specific for activated coagulation factor X (Xa). A comparison of all of these probes indicated that annexin V was the most sensitive for the detection of platelet activation.

Test specificity is of primary importance in attempting to diagnose HIT. As shown in FIG. 1, the flow cytometry assay of the invention for detection of thrombocytopenia was found to be highly specific for heparin. In a specific embodiment, platelets were incubated with heparin and plasma samples for one hour at room temperature and with P2 antibody and annexin V for 30 minutes at room temperature. FIG. 1 presents the results obtained with the flow cytometry assay for plasma from normal individuals (NC, normal controls) and plasma from patients clinically suspected of having HIT (patient). The background fluorescence obtained for the normal control is not dependent on the presence of heparin and therefore is used to constitute a baseline or control value of fluorescence for a control or negative reaction. In contrast, aliquots from a HIT patient sample show increased fluorescence, above normal control values, for samples comprising therapeutic concentrations of heparin (i.e., 0.1 and 0.3 IU/ml), but exhibit only baseline fluorescence equal to normal control levels for samples without heparin and for samples containing a high heparin concentration (e.g., 100 IU/ml).

A "positive control" sample is included in each assay performance as a reference control. As shown in FIG. 1, the magnitude of immunofluorescence for the patient suspect of HIT ("patient") was similar to that obtained for a patient known to have HIT. Other controls may also be included in the assay procedure. For example, to ascertain an approximate, maximal level of fluorescence to be expected f[]or plasma from a HIT patient, a control comprising an ionophore, such as the calcium ionophore A23817, or other such similar compound which acts to stimulate maximally the activation and aggregation of platelets, may be used to obtain by independent means a maximal level of fluorescence for the flow cytometry assay and, in so doing, to establish a "quality control" check for reagent use and the viability of the platelet preparation during the assay.

Thus, the flow cytometry method demonstrates specificity for plasma from patients with HIT by showing a positive fluorescence due to annexin V binding to activated platelets. Platelets become activated in this assay by interaction with an immune complex induced by heparin (therapeutic concentrations) and plasma from a HIT patient. Annexin V binds specifically to activated platelets with high affinity. Therefore, the flow cytometry method of this invention detects specifically activated platelets wherein the activation is dependent on the presence of a therapeutic concentration of heparin and, hence, represents in vitro the in vivo manifestation of platelet transformation by a heparin immune complex leading to thrombocytopenia. Significantly, the flow cytometry method for detection of HIT measures a functional state of a cell rather than only a specific biochemical marker on a cell.

The flow cytometry assay of the invention was compared directly to the art standard serotonin-release assay and found to be not only more sensitive but also a faster and easier assay to perform. In addition, the flow cytometry assay does not require the use of radioactivity and therefore can be performed in any routine laboratory on site. As shown in Table 1, aliquots of each plasma sample were tested in both the flow cytometry assay as well as in the radioactive serotonin release assay.

TABLE 1

Comparison of flow cytometry*[1] and the serotonin release assay for detection of HIT

| | Determination of HIT | | | |
|---|---|---|---|---|
| | Flow Cytometry Assay | | Serotonin Release Assay | |
| Patient | Positive | Negative | Positive | Negative |
| 22 patients with HIT | 17 | 3 | 17 | 3 |
| | 1 | 0 | 0 | 1 |
| | 0 | 1 | 1 | 0 |
| | (18) | (4) | (18) | (4) |
| 4 normals without HIT | 0 | 4 | 0 | 4 |

[1]( ) indicates a subtotal of preceding column numbers.
*Incubation time for the heparin-dependent immune reaction was 60 minutes at room temperature and for the labeled marker binding reaction was 30 minutes at room temperature.

As shown in Table 1, a total of 22 plasma samples from patients with clinically-suspected HIT (a total of 67 tests) and 4 normal individuals (a total of 18 tests) were assayed by flow cytometry for the detection of HIT. These samples were also tested, in parallel, with the radioactive serotonin release assay (a total of 50 tests for patients and 8 tests for normals). Normal controls gave highly reproducible results which correlated well with the results of the serotonin release assay (r=0.944). For the flow cytometry assay, the mean value of fluorescence for normal controls, as compared to samples without heparin or with a high concentration of heparin, was calculated to be 1.5±0.4 and the range was 0.5–1.9. For the serotonin release assay, the mean value obtained for release of $^3$H-serotonin for the normal controls, in comparison to samples with no heparin, was 2.5±1.2 with a range of 1.3–4.0. Thus, the flow cytometry method showed a lower background level compared to the serotonin release assay.

Of the 22 patients with HIT, 17 were positive (having fluorescence values greater than the range and standard deviation of the normal control) and three were negative with both the flow cytometry assay and the serotonin release assay. One was positive by flow cytometry and negative by the serotonin release assay, and one was negative by flow cytometry and positive by the serotonin release assay. These two patients, however, had borderline results with both methods.

Among the 17 patients positive with both methods, the flow cytometry assay was more sensitive than the serotonin release assay in 15, equally sensitive in one, and less sensitive in one, showing a mean of 5.3-fold increase in fluorescence (binding of annexin V) as compared to 2.9-fold increase in serotonin release, when compared to corresponding values for normal controls in both assay methods. Thus, the flow cytometry method not only reduced background signals but, consequently, increased both the sensitivity and specificity of the assay by improving the resolution between positive and negative samples.

Further, the flow cytometry assay was optimized by shortening the time of incubation for formation of the heparin-dependent immune reaction and for the binding of labeled markers to platelets. In a particular embodiment of the invention, the flow cytometry assay was conducted under more optimized experimental conditions wherein the incubation time for interaction with heparin was shortened from one hour to 30 minutes and incubation with P2 anti-GPIIb/IIIa antibody from 30 minutes to 15 minutes at room temperature, reducing the total time for carrying out the assay to approximately 45 minutes. Thus, this flow cytometric assay of the invention allowed a determination as to the presence or absence of HIT to be made within 1.5 to 2 hours after obtaining a blood sample from a suspect patient.

For patients who develop HIT while being treated with a standard preparation of heparin, an alternate anticoagulant therapy, e.g., low molecular weight heparin, heparinoids, and the like, is prescribed. Unfortunately, in many patients with HIT the circulating anti-heparin antibodies crossreact with these alternate heparin-like molecules, resulting in adverse reactions. Despite its obvious clinical importance, there is presently no available assay for immediate assessment of the compatibility of low molecular weight heparins or heparinoids, or the like, with the patient's blood.

The flow cytometric method of this invention provides a rapid method for assessing the compatibility of a patient's blood with heparin-like molecules. In a particular embodiment of the invention, low molecular weight heparin Lovenox® [Rhone-Poulenc Rorer Inc., Collegeville, Pa.] having an average molecular weight of approximately 4500 daltons was interacted with platelets in the presence of plasma samples obtained from 16 patients with clinically suspected HIT. Thirteen of the patients gave positive reactions in the flow cytometry assay with standard heparin as well as the low molecular heparin, indicating that low molecular weight heparin was incompatible as an alternate therapy. These results are consistent with recent reports of thrombosis associated with severe morbidity and mortality in HIT patients who received low molecular weight heparin therapy without prior testing of its compatibility. Three of the sixteen patients clinically suspected of having HIT were diagnosed with the flow cytometry assay to be negative for HIT and these same three patients also gave negative reactions with the low molecular weight heparin. Thus, the results obtained with the flow cytometry method of the invention were concordant not only between heparin and a low molecular weight molecule but, in addition, confirmed the results obtained with the serotonin release assay.

FIGS. 2A–2E illustrate the comparison between low molecular weight heparin and standard heparin in the flow cytometry assay for the detection of HIT in plasma samples from 16 different patients. FIGS. 2A–2D demonstrate positive reactivity as measured by increased fluorescence in the flow cytometry assay for patients 1–13, indicating a positive diagnosis of HIT for patients 1–13. In contrast, FIG. 2E demonstrates negative reactivity in the flow cytometry assay for patients 14, 15 and 16 in comparison to the positive reaction obtained from patient 3. According to the results of the flow cytometry assay (and confirmed with the serotonin release assay), patients 14, 15 and 16 do not have HIT; they show immunologic tolerance for low molecular weight heparin, and they do not indicate incompatibility of low molecular weight heparin for use as an alternate therapeutic for these patients (patients 14, 15 and 16).

As shown in FIGS. 2A–2E, low molecular weight heparin behaves very similarly to heparin for all patient plasma samples, whether testing positive or negative in the flow cytometry assay. The flow cytometry assay appears as highly sensitive and as highly reproducible for the low molecular weight heparin as for the standard heparin, giving approximately the same high levels of fluorescence above normal control levels for both compounds at each concentration tested and for each patient tested. The level of reaction with low molecular weight heparin is fully concordant with that obtained with standard heparin for each plasma sample from thirteen different patients showing positive diagnoses of HIT and three patients showing negative diagnoses of HIT. Such clear cut results obtained with the flow cytometry assay for assessment of the compatibility of a heparin-like molecule allow a critical and immediate decision to be made unambiguously for the continued management and care of a patient with HIT.

Testing for the compatibility of heparinoids or other heparin-like molecules with a patient's blood can also be carried out with the flow cytometric assay. This test can be performed simultaneously with the flow cytometry assay for the detection of HIT. Thus, this invention provides a functional assay that not only permits the diagnosis of HIT but also provides an assay for the assessment of an alternate therapy comprising a heparin-like molecule. The flow cytometry assay detects the presence of anti-heparin antibodies in the patient's blood capable of crossreacting with the heparin-like molecule. In this way, this invention is relevant to the formation of diagnostic decisions required for the correct management of a patient treated with heparin.

The invention also contemplates the preparation of a kit useful for the detection of HIT in a plasma sample. Such a kit comprises in a package containers holding buffered medium, and heparin at different concentrations including (a) zero heparin, (b) a therapeutic concentration of heparin ranging from approximately 0.001 to approximately 1.0 IU/ml, and (c) a high concentration of heparin ranging from approximately 10.0 to approximately 1000 IU/ml. The kit further comprises a first labeled compound to react specifically with platelets and a second labeled compound to react specifically with activated platelets. In a preferred embodiment of the invention, aliquots of the plasma sample are reacted with platelets in the presence of heparin at a concentration of 0, 0.1, 0.3 and 100.0 IU/ml and then further reacted with phycoerythrin-labeled antibody against platelet glycoprotein IIb/IIIa for platelet identification and with directly fluoresceinated recombinant-human annexin V for identification of activated platelets. These specific labeled compounds may be substituted with other labeled compounds such that in combination they will allow specific identification of (a) platelets and (b) activated platelets. The kit of the present invention, when used according to the method of the invention in conjunction with a flow cytometer, is useful in determining the presence or absence of HIT in a plasma sample. Thus, the kit according to the invention has utility in screening plasma samples from patients treated with heparin for the presence of HIT.

The invention also contemplates the preparation of a kit useful for the assessment of compatibility of a heparin-like molecule as an alternate therapy for patients with HIT. Such a kit comprises in a package containers holding buffered medium, and a heparin-like molecule at different concentrations including (a) zero heparin-like molecule, (b) a therapeutic concentration of heparin-like molecule ranging from approximately 0.001 to approximately 1.0 IU/ml, and (c) a high concentration of a heparin-like molecule ranging from approximately 10.0 to approximately 1000 IU/ml. The kit further comprises a first labeled compound to react specifically with platelets and a second labeled compound to react specifically with activated platelets. In a preferred embodiment, aliquots of the plasma sample are reacted with platelets in the presence of a low molecular weight heparin or a heparinoid at a concentration of 0, 0.1, 0.3 and 100 IU/ml, and then further reacted with phycoerythrin-labeled antibody against platelet glycoprotein IIb/IIIa for platelet identification and with directly fluoresceinated recombinant-human annexin V for identification of activated platelets. The kit of the present invention, when used according to the method of the invention in conjunction with a flow cytometer, is useful in detecting the presence of anti-heparin antibodies crossreacting with platelets in the presence of a test heparin-like molecule. Thus, the kit according to the invention has utility in assessing the compatibility of a heparin-like molecule for use as an alternate therapy in patients having HIT.

Further, the invention also contemplates the preparation of a kit useful for the simultaneous detection of both HIT and the compatibility of a heparin-like molecule for use as an alternate therapy. In such a combination kit useful for simultaneous determinations, the ingredients of each of the single kits are combined in a single package such that analyses can be performed at the same time not only for HIT but also for compatibility of a proposed alternate therapy.

The present invention also contemplates a mepacrine (quinacrine) release assay with flow cytometry for the detection of HIT and for the assessment of compatibility of a heparin-like molecule for use as an alternate therapy in a patient having HIT. In this assay, platelets are first preloaded with mepacrine, a vividly fluorescent molecule, and then reacted with plasma from a patient suspected of HIT in the presence of different concentrations of heparin (zero, one or more therapeutic concentrations and a high concentration). At therapeutic concentrations of heparin and in the presence of plasma from a HIT patient, platelets undergo activation and aggregation—conditions which cause the platelets to release the preloaded mepacrine. By standard flow cytometry analysis, the fluorescence associated with the platelet population is utilized to determine the level of uptake or release of mepacrine from the platelets. A decrease in fluorescence is correlated with platelet activation.

Figure 3:
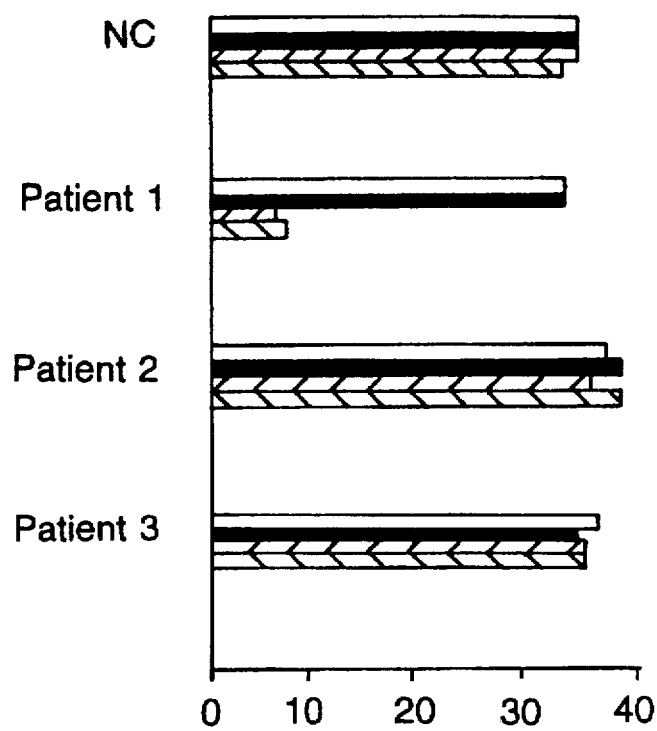
FIG. 3 illustrates the use of a mepacrine release assay with flow cytometry for the detection of HIT in plasma samples from patients suspected of having HIT and from normal controls. "NC" refers to a normal control plasma from an individual without HIT. "Patient" refers to a plasma sample from a patient suspected of having HIT.

As shown in FIG. 3, plasma samples from a normal control gave approximately maximal fluorescence at all concentrations of heparin, indicating that the platelets were not activated by any concentration of heparin in the presence of normal plasma and that the normal plasma did not contain heparin-induced antibodies. The results for three patients suspected of having HIT were variable.

Samples of plasma from patient 1 (as shown in FIG. 3) exhibited a decreased fluorescence in the presence of therapeutic concentrations of heparin (0.1 and 03 U/ml), indicating the presence of activated platelets under these assay conditions and a diagnosis of HIT for patient 1. These results indicating a positive HIT condition for patient 1 with the mepacrine release assay confirmed the positive HIT diagnosis obtained with the flow cytometry assay of the invention.

In contrast, plasma samples from patients 2 and 3 (as illustrated in FIG. 3) showed in the mepacrine release assay for all experimental conditions and heparin concentrations a level of fluorescence comparable to that obtained for the normal control plasma, indicating that patients 2 and 3 did not have HIT. However, these same patients 2 and 3 were diagnosed with HIT in the flow cytometry assay of the invention as well as with the serotonin release assay. Thus, although the mepacrine release assay with flow cytometry is selectively responsive to therapeutic concentrations of heparin as diagnostic of HIT, the mepacrine assay does not appear to be as sensitive as the flow cytometry assay of the invention for the detection of HIT.

Figure 4:
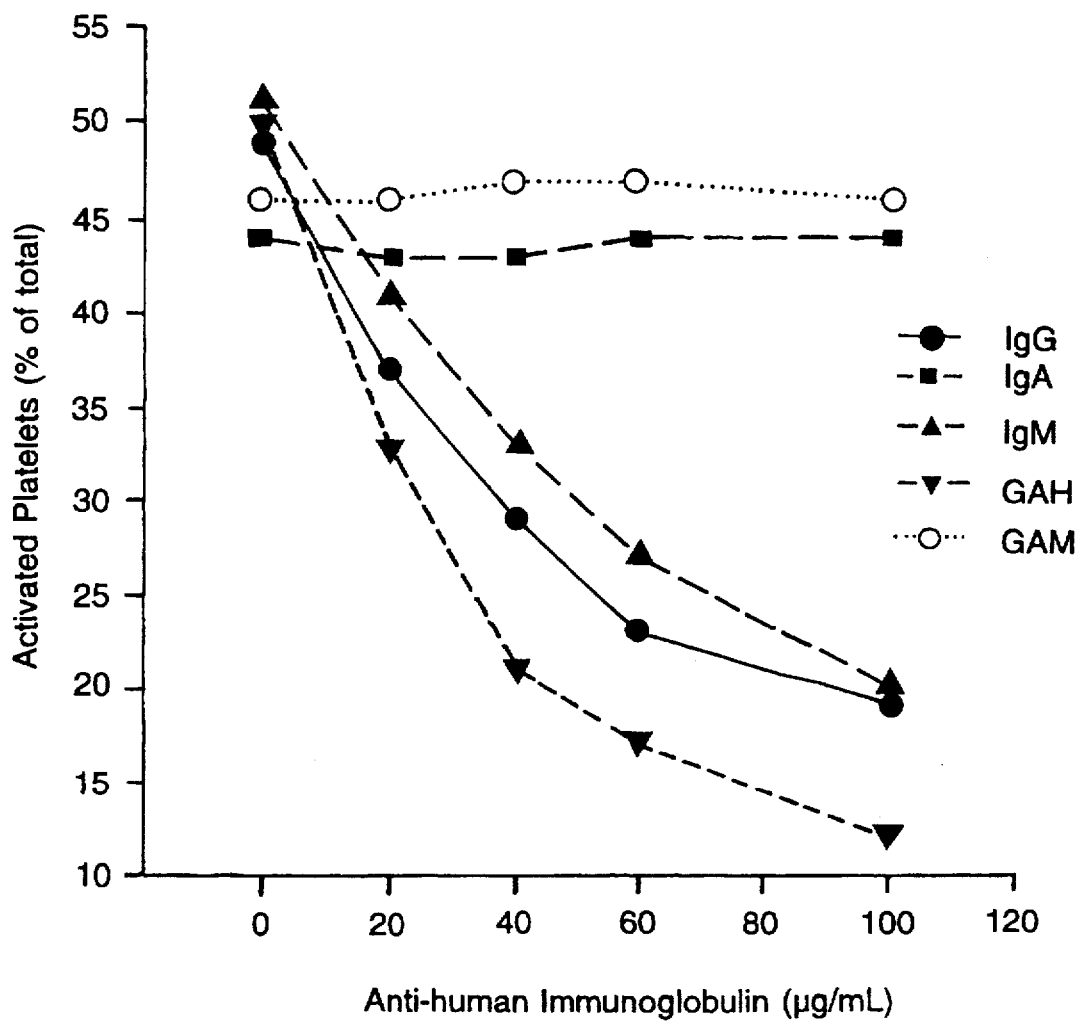
FIG. 4 illustrates the neutralization of platelet activation upon incubating HIT patient plasma with anti-human immunoglobulin.

Direct evidence for an antibody-mediated mechanism responsible for platelet activation was provided by a complementary test included in the flow cytometry assay. This test comprised the step of pre-incubation of patient plasma with anti-human immunoglobulin in order to neutralize anti-heparin antibodies present in HIT patient plasma and, thus, to eliminate formation of heparin-immune complex responsible for platelet activation. As shown in FIG. 4, platelet activation was neutralized in a dose-response manner by goat anti-human (GAH) immunoglobulins and goat anti-human IgG and IgM preparations, but not by goat anti-human IgA nor by goat anti-mouse (GAM) preparations. Goat anti-mouse antibodies were used as a control to rule out non-specific inhibition of platelet activation induced by goat antibodies.

Inclusion of this complementary test within the flow cytometry assay is useful not only in detecting anti-heparin antibodies but also in detecting the presence of antibodies cross-reacting with heparin-like molecules, such as low molecular weight heparin, heparinoids and the like. Thus, the flow cytometry assay in combination with the complementary test is capable of providing in one simple assay, with enhanced sensitivity, reliability and rapidity, the results previously obtainable only by performing two different assays, i.e., the SRA assay and the ELISA assay.

It will be apparent to those of ordinary skill in the art that alternative method, reagents, procedures and techniques other than those specifically detailed herein can be employed or readily adapted to practice the detection methods of this invention. Such alternative methods, reagents, procedures and techniques are within the spirit and scope of this invention.

The methods of this invention are further illustrated in the following non-limiting Examples. All abbreviations used herein are standard abbreviations in the art. Specific procedures not described in detail in the Examples are well-known in the art.

EXAMPLES

Example 1

Flow cytometry assay.

Platelet-rich plasma (PRP) was prepared from normal controls with O or A, B-matched blood type (or from patient blood when possible) by centrifuging whole blood at 900 rpm for five minutes at room temperature. The platelet count was adjusted to $300,000/\mu l$. Stimulation with the $Ca^{++}$-ionophore A23817 (5 $\mu$M) was used to assess the viability of the platelet preparation during the assay.

Test plasma (plasma) was prepared from patient whole blood by centrifuging at 2500 g for thirty minutes at room temperature. Platelets are obtained from whole blood and handled with gentle care and minimal manipulation throughout the assay procedure to prevent spontaneous activation of the platelets. Samples of test plasma were used fresh or stored at $-70°$ C.

Aliquots (20 $\mu$l) of plasma either from a patient suspected of having HIT or from a normal patient control (NC) were incubated in the presence of PRP (70 $\mu$l) and heparin (10 $\mu$l) to give different final concentrations of heparin, i.e., none, one or more therapeutic concentrations (0.1 and 0.3 IU/ml) and a high concentration (100 IU/ml) of heparin. After a 30 minute to one hour incubation at room temperature with occasional gentle mixing, aliquots from each sample were incubated for fifteen to thirty minutes with phycoerythrin (PE)-labeled antibody against platelet glycoprotein IIb/IIIa for platelet identification (P2 clone, [Immunotech, Inc. (AMAC CO.), Westbrook, Me.] and with directly fluoresceinated recombinant-human annexin V protein (Kowa Co., Tokyo, Japan) in 0.02M HEPES buffer with 2.5 mM $CaCl_2$ to react with activated platelets under assay conditions essentially as described in Thiagarajan et al. (1990) J. Biol. Chem. 265:17420–17423.

Activated platelets were detected by standard flow cytometry analysis using FACscan analyzer (Becton Dickinson, San Jose, Calif.). The platelet population was identified by light scatter and the specific red-fluorescence of phycoerythrin, and was selected by an electronic gate. Gated platelets were then assessed for activation by measurement of the specific green-fluorescence of annexin V, the level of which directly relates to the degree of activation. The total binding of annexin is calculated by multiplying the mean fluorescence level by the total number of activated (annexin positive) platelets. The results were then compared to the internal control samples (e.g., with zero and 100 IU/ml heparin) to assess specificity and were related to the normal controls (NC) to determine the magnitude of activation.

Example 2

Serotonin release assay.

The serotonin release assay was performed essentially as described in Kelton et al. (1994) Blood 83:3232–3239.

Example 3

Mepacrine (Quinacrine) release assay with flow cytometry for detection of HIT.

Platelets, prepared as a platelet rich plasma (PRP) as described in Example 1, were preloaded with mepacrine (quinacrine), a vividly fluorescent molecule, using conventional uptake conditions known in the art and as exemplified in the serotonin release assay of Kelton et al. (1994) supra (referenced in Example 2 above). Mepacrine is rapidly taken up and localized in dense granules of platelets [Wall et al. (1995) British J. Haematology 89:380–385].

Aliquots of plasma either from a patient suspected of having HIT or from a normal patient control (NC) were incubated at room temperature for 60 minutes in the presence of PRP and heparin to give final heparin concentrations of (a) zero heparin, (b) a therapeutic heparin concentration (0.1 and 0.3 IU/ml), and (c) a high heparin concentration (100 IU/ml). Both the uptake and release of mepacrine in platelets were readily detected by flow cytometry.

The platelet population was identified in standard flow cytometry analysis by the fluorescence of the mepacrine taken up by the non-activated platelets. Activated platelets were detected by the release of mepacrine and the consequent decrease in fluorescence. Total fluorescence for patient plasma samples was compared to corresponding samples of normal controls. Additional internal controls, for example, collagen and the calcium ionophore A23817, pretested with PRP to produce full activation and aggregation of the platelets, were included in the assay to establish independently the fluorescence limits for non-activated and activated platelets.

Example 4

Clinical evaluation of HIT

As reviewed by George et al. in the American Society of Hematology Education Program, Dec. 2–6, 1994, Nashville, Tenn., the clinical picture of patients with HIT comprises the recognition of HIT and the detection of thrombotic complications.

Most clinical studies of HIT define the syndrome according to the following criteria: (1) a decrease in platelet counts to values below $150 \times 10^9/l$ (or $100 \times 10^9/l$) during heparin treatment in patients who originally had normal platelet counts; (2) normalization of platelet counts within several days of discontinuation of heparin; (3) absence of any other potential etiology for the thrombocytopenia. In clinical practice, HIT should be suspected whenever a patient receiving any form of heparin becomes thrombocytopenic or develops an unexplained significant decrease in platelet counts (i.e., >40%) even though levels remain above 150× 10⁹/l. Apparent thrombocytopenia due to platelet clumping in vitro can be excluded by examination of the peripheral smear.

Arterial and venous thromboses have been estimated to occur in as many as 20% of patients with HIT, although accurate determination of the incidence is quite difficult and may vary with the population being studied. Sudden thrombotic events such as myocardial infarction, peripheral arterial thrombosis, and pulmonary emboli are often not initially recognized as a complication of heparin because of the patient's underlying illness. Furthermore, some patients with heparin-induced antibodies will have thrombosis in the absence of thrombocytopenia. This may be due to the rapid onset of the thrombotic manifestation or to increased platelet production.

Clinical conditions that increase the risk of thrombosis in patients with HIT are sepsis, recent surgery, and atherosclerotic vascular disease. The common denominators for these patients are high levels of circulating cytokines such as IL-6, pre-existing endothelial damage due to invasive procedures, and activated platelets, all of which promote arterial and venous thromboembolism in the presence of heparin immune complexes. In patients who have not previously received heparin, the interval between initiation of anticoagulation and thrombosis is usually about nine days (range, 4–15) and decreases to five days (range, 2–9 days) for those with a previous exposure.

Heparin should be discontinued as soon as the diagnosis of HIT is strongly considered. This recommendation is made because thrombotic complications cannot be predicted in a given patient, and serious morbidity, often resulting in death, has been reported in 50% of patients with HIT who develop thrombosis. The management of patients with HIT and thrombosis is based on the underlying clinical condition for which the patient is receiving anticoagulation, as well as the availability of alternate anticoagulants.

At this time, tests for heparin-induced antibodies are performed in reference laboratories. For example, the SRA assay, dependent on the use of a radioactively labeled substrate, must be performed in a reference laboratory which may result in a delay of approximately one week before the results of the assay are obtained. There are no commercially available test kits, and sera that have been accepted as testing positive and negative for heparin-induced antibodies are not available for assay standardization. The true sensitivity and specificity are therefore difficult to establish. For example, the ELISA assay detects only the presence of antibody which may or may not indicate HIT. At the present time, the initial diagnosis of HIT and management decisions are made on a clinical basis. Patient sera may be sent to reference laboratories to confirm a clinical diagnosis of HIT retrospectively, to determine if re-exposure to heparin can occur during a surgical procedure, or to identify antibodies that are crossreactive with low molecular weight heparin or heparinoid.

Example 5

Detection of reactive anti-heparin antibodies in HIT patients by flow cytometry.

The flow cytometry assay was carried out essentially as described in Example 1 except for the inclusion of an additional step comprising a complementary test to confirm the presence in the patient plasma of immunoglobulin available for formation of a heparin-immuno complex responsible for platelet activation.

Aliquots of plasma either from a patient suspected of having HIT or from a normal patient control were pre-incubated for 30 minutes at room temperature with increasing doses of an anti-human immunoglobulin preparation. The pre-incubated plasma was then incubated with PRP and heparin followed by the addition of anti-platelet GPIIb/IIIa antibody (for immune detection of platelets) and annexin V (for detection of activated platelets) according to the procedure described in Example 1 for the flow cytometry assay.

Platelet activation was neutralized in a dose-response manner in patient plasma that was pre-incubated with goat anti-human immunoglobulins [Organon-Technika, West Chester, Pa.]. In particular, goat anti-human IgG and/or IgM preparations [Sigma Chemical Company, St. Louis, Mo.] were effective, whereas goat anti-human IgA and goat anti-mouse (GAM) preparations were ineffective in neutralizing platelet activation (see FIG. 4). A single dose (approximately 100 μg/ml) of a goat anti-human antibody preparation is sufficient to produce maximal inhibition of platelet activation. Goat anti-mouse immunoglobulins were used as a control to rule out non-specific effects due to goat antibodies.

Inclusion of this complementary test in the flow cytometry assay provided direct evidence for both the presence of specific antibodies in the patient plasma and for the functional capacity of these specific antibodies to interact with and activate platelets in the presence of therapeutic doses of heparin.

I claim:

1. A flow cytometry assay for the detection of heparin-induced thrombocytopenia in a patient treated with heparin, said assay comprising the steps of:
   (a) obtaining a plasma sample from said patient;
   (b) interacting aliquots of said plasma sample with platelets from a normal donor in the presence of said heparin;
   (c) incubating said plasma-platelets-heparin interaction of step (b) with a first labeled compound specific for platelets and with a second labeled compound specific for activated platelets;
   (d) detecting by flow cytometry
      (i) said platelets labeled with said first labeled compound, and
      (ii) said activated platelets labeled with said second labeled compound; and
   (e) diagnosing a condition of heparin-induced thrombocytopenia for said patient upon detection in step (d) of a level of said activated platelets labeled with said second labeled compound that is elevated compared to a corresponding level of said second labeled compound in normal control plasma or, in the alternative, diagnosing a negative condition of heparin-induced thrombocytopenia.

2. The assay according to claim 1 wherein said heparin is present in different aliquots of said plasma sample at concentrations including (a) zero heparin, (b) a therapeutic concentration of heparin of between approximately 0.01 and approximately 1.0 IU/ml, and (c) a high concentration of heparin of between approximately 10 and approximately 1000 IU/ml.

3. The assay according to claim 1 wherein said interaction of step (b) is carried out at room temperature for between approximately 30 and approximately 60 minutes.

4. The assay according to claim 1 wherein said incubation of step (c) is carried out at room temperature for between approximately 15 and approximately 30 minutes.

5. The assay according to claim 1 wherein said first labeled compound is a labeled antibody against a platelet surface protein.

6. The assay according to claim 1 wherein said first labeled compound is a labeled antibody against platelet glycoprotein IIb/IIIa.

7. The assay according to claim 5 wherein said antibody is the P2 monoclonal antibody.

8. The assay according to claim 1 wherein said first labeled compound is labeled with phycoerythrin or fluorescein isothiocyanate.

9. The assay according to claim 1 wherein said second labeled compound is a compound exhibiting an increased binding, of at least about 300-fold, to activated platelets over resting state platelets.

10. The assay according to claim 1 wherein said second labeled compound is annexin V.

11. The assay according to claim 10 wherein said annexin V is a recombinant human protein.

12. The assay according to claim 1 wherein said second labeled compound is labeled with fluorescein isothiocyanate or phycoerythrin.

13. The assay according to claim 1 wherein said platelets, detected by a specific first signal of said first labeled compound, are then screened for a specific second signal of said second labeled compound.

14. The assay according to claim 1 further comprising the step of pre-incubating an aliquot of said plasma sample of step (a) with an amount of anti-human immunoglobulin sufficient to react with anti-heparin antibodies in said plasma sample such that platelet activation by said plasma sample in the presence of heparin as detected in steps (b) to (e) is neutralized.

15. The assay of claim 14 wherein said anti-human immunoglobulin is selected from the group consisting of a goat anti-human immunoglobulin preparation, a goat anti-human IgG preparation, and a goat anti-human IgM preparation.

16. A flow cytometric assay for the detection of heparin-induced thrombocytopenia in a patient treated with heparin, said assay comprising the steps of:
   (a) obtaining a plasma sample from said patient;
   (b) interacting aliquots of said plasma sample with platelets form a normal donor in the presence of said heparin at concentrations of 0, 0.1, 0.3 and 100 IU/ml for approximately 30 to 60 minutes at room temperature;
   (c) incubating said plasma-platelet-heparin interactions of step (b) with phycoerythrin-labeled P2 monoclonal antibody against platelet glycoprotein IIb/IIIa to label platelets and with directly fluoresceinated annexin V protein to label activated platelets for approximately 15 to 30 minutes at room temperature;
   (d) detecting by flow cytometry
      (i) said platelets by said phycoerythrin label and
      (ii) said activated platelets by said annexin V label; and
   (e) diagnosing a condition of heparin-induced thrombocytopenia for said patient upon detection in step (d) of a level of said activated platelets that is elevated compared to a corresponding level of activated platelets in normal control plasma or, in the alternative, diagnosing a negative condition of heparin-induced thrombocytopenia.

17. A flow cytometry assay to assess the compatibility of a heparin-like molecule for use as an alternate therapy for a patient having heparin-induced thrombocytopenia, said assay comprising the steps of:
   (a) obtaining a plasma sample from said patient;
   (b) interacting aliquots of said plasma sample with platelets from a normal donor in the presence of said heparin-like molecule;
   (c) incubating said plasma-platelet-heparin-like molecule interactions of step (b) with a first labeled compound specific for platelets and with a second labeled compound specific for activated platelets;
   (d) detecting by flow cytometry
      (i) said platelets labeled with said first labeled compound and
      (ii) said activated platelets labeled with said second labeled compound; and
   (e) diagnosing a condition of incompatibility for the use of said heparin-like molecule as an alternate therapy for said patient having heparin-induced thrombocyto-penia upon detection in step (d) of a level of activated platelets labeled with said second labeled compound that is elevated compared to a corresponding level of activated platelets in normal control plasma or, in the alternative, a condition of compatibility.

18. The assay according to claim 17 wherein said heparin-like molecule is a low molecular weight heparin or a heparinoid.

19. The assay according to claim 18 wherein said low molecular weight heparin has an average molecular weight of approximately 4500 daltons.

20. The assay according to claim 18 wherein said heparinoid is heparamine.

21. The assay according to claim 17 wherein said heparin-like molecule is present in different aliquots of said plasma sample at concentrations including (a) zero heparin-like molecule, (b) a therapeutic concentration of said heparin-like molecule of between approximately 0.01 and approximately 1.0 IU/ml, and (c) a high concentration of said heparin-like molecule of between approximately 10 to approximately 1000 IU/ml.

22. The assay according to claim 17 wherein said first labeled compound is a phycoerythrin-labeled antibody against platelet glycoprotein IIb/IIIa.

23. The assay according to claim 17 wherein said second labeled compound is a directly fluoresceinated annexin V.

24. The assay according to claim 17 further comprising the step of pre-incubating an aliquot of said plasma sample of step (a) with an amount of anti-human immunoglobulin sufficient to react with anti-heparin antibodies in said plasma sample such that platelet activation by said plasma sample in the presence of heparin as detected in steps (b) to (e) is neutralized.

25. A kit useful for the detection of heparin-induced thrombo-cytopenia in a plasma sample comprising:
   a buffered medium and said heparin;
   a first labeled compound specific for platelets; and
   a second labeled compound specific for activated platelets.

26. The kit according to claim 25, wherein said heparin is present in different aliquots of said buffered medium at concentrations including (a) zero heparin, (b) a therapeutic concentration of heparin of between approximately 0.01 and approximately 1.0 IU/ml, and (c) a high concentration of heparin of between approximately 10 and approximately 1000 IU/ml.

27. The kit according to claim 25, wherein said first labeled compound is a phycoerythrin-labeled antibody against platelet glycoprotein IIb/IIIa.

28. The kit according to claim 25, wherein said second labeled compound is a directly fluoresceinated annexin V.

29. The kit according to claim 25 further comprising an anti-human immunoglobulin preparation.

30. A kit useful for the assessment of compatibility of a heparin-like molecule for use as an alternate therapy for a patient having heparin-induced thrombocytopenia comprising:

a buffered medium and said heparin-like molecule;

a first labeled compound specific for platelets; and a second labeled compound specific for activated platelets.

31. The kit according to claim 30, wherein said heparin-like molecule is a low molecular weight molecule or a heparinoid.

32. The kit according to claim 30, wherein said heparin-like molecule is present in different aliquots of said buffered medium at concentrations including (a) zero said heparin-like molecule, (b) a therapeutic concentration of said heparin-like molecule of between approximately 0.01 and approximately 1.0 IU/ml, and (c) a high concentration of said heparin-like molecule of between approximately 10 and approximately 1000 IU/ml.

33. The kit according to claim 30, wherein said first labeled compound is a phycoerythrin-labeled antibody against platelet glycoprotein IIb/IIIa.

34. The kit according to claim 30, wherein said second labeled compound is a directly fluoresceinated annexin V.

35. The kit according to claim 30, further comprising an anti-human immunoglobulin preparation.

36. A combination kit useful for the simultaneous detection of heparin-induced thrombocytopenia in a plasma sample and for the assessment of compatibility of a heparin-like molecule for use as an alternate therapy for a patient having heparin-induced thrombocytopenia comprising:

a buffered medium and said heparin;

a buffered medium and said heparin-like molecule;

a first labeled compound specific for platelets; and a second labeled compound specific for activated platelets.

37. A flow cytometry assay for the detection of heparin-induced thrombocytopenia in a patient treated with heparin, said assay comprising the steps of:

(a) obtaining a plasma sample from said patient;

(b) interacting aliquots of said plasma sample with platelets from a normal donor in the presence of said heparin;

(c) incubating said plasma-platelet-heparin interaction of step (b) with a labeled compound specific for activated platelets;

(d) detecting by flow cytometry said activated platelets labeled with said labeled compound; and (e) diagnosing a condition of heparin-induced thrombocytopenia for said patient upon detection in step (d) of a level of said activated platelets labeled with said labeled compound that is elevated compared to a corresponding level of said labeled compound in normal control plasma or, in the alternative, diagnosing a negative condition of heparin-induced thrombocytopenia.

38. A flow cytometry assay to assess the compatibility of a heparin-like molecule for use as an alternate therapy for a patient having heparin-induced thrombocytopenia, said assay comprising the steps of:

(a) obtaining a plasma sample from said patient;

(b) interacting aliquots of said plasma sample with platelets from a normal donor in the presence of said heparin-like molecule;

(c) incubating said plasma-platelet-heparin-like molecule interactions of step (b) with a labeled compound specific for activated platelets;

(d) detecting by flow cytometry said activated platelets labeled with said labeled compound; and (e) diagnosing a condition of incompatibility for the use of said heparin-like molecule as an alternate therapy for said patient having heparin-induced thrombo-cytopenia upon detection in step (d) of a level of activated platelets labeled with said labeled compound that is elevated compared to a corresponding level of activated platelets in normal control plasma or, in the alternative, a condition of compatibility.

* * * * *

UNITED STATES PATENT AND TRADEMARK OFFICE
CERTIFICATE OF CORRECTION

PATENT NO. : 5,763,201
DATED : Jun. 9, 1998
INVENTOR(S) : Aaron Tomer

It is certified that error appears in the above-identified patent and that said Letters Patent is hereby corrected as shown below:

In claim 16, column 21, line 41, "form" should read --from--.

At column 1, line 66, "patient" should read --patients--.

At column 8, line 7, "art" should read --an--.

At column 8, line 32, the semicolon after "50% or less" should be deleted.

At column 9, line 23, "GPIb" should read --Ib--.

At column 10, line 13, the period after "After a" should be deleted.

At column 10, line 63, "GP]IIb/IIIa" should read --GPIIb/IIIa--.

At column 11, lines 5-6, "GP'[IIb/IIIa" should read --GPIIb/IIIa--.

At column 12, line 28, "suspect of" should read --suspected of having--.

At column 12, line 33, "f[]or" should read --for--.

At column 16, line 43, "03 U/ml" should read --0.3 IU/ml--.

At column 17, line 22, "method" should read --methods--.

Signed and Sealed this

Tenth Day of November 1998

Attest:

BRUCE LEHMAN

*Attesting Officer*     *Commissioner of Patents and Trademarks*